United States Patent
Houde et al.

(12) 
(10) Patent No.: US 6,976,974 B2
(45) Date of Patent: Dec. 20, 2005

(54) ROTARY MANIFOLD SYRINGE

(75) Inventors: Eric Houde, Saratoga Springs, NY (US); Mark Van Diver, Argyle, NY (US); Scott Diamond, Fort Edward, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 374 days.

(21) Appl. No.: 10/278,663

(22) Filed: Oct. 23, 2002

(65) Prior Publication Data

US 2004/0082904 A1 Apr. 29, 2004

(51) Int. Cl.[7] .......................... A61M 1/00; F17D 3/00
(52) U.S. Cl. ................... 604/32; 137/625.21
(58) Field of Search ................... 604/30, 32, 80, 604/181, 187, 191, 246, 248, 257, 258, 284, 604/533, 534, 535, 537, 538, 539; 137/625.21, 137/625.22, 625.23, 625.24, 625.4, 625.41, 137/625.42, 625.46, 602

(56) References Cited

U.S. PATENT DOCUMENTS

| | | | |
|---|---|---|---|
| 3,384,372 A | 5/1968 | Dickens | |
| 4,819,653 A | 4/1989 | Marks | |
| 5,104,387 A | 4/1992 | Pokorney et al. | |
| 5,168,901 A | 12/1992 | Marks | |
| 5,232,024 A | 8/1993 | Williams | |
| 5,515,851 A | 5/1996 | Goldstein | |
| 6,135,153 A | 10/2000 | Cleland, Sr. et al. | |
| 6,158,467 A * | 12/2000 | Loo | 137/625.47 |
| 6,457,488 B2 * | 10/2002 | Loo | 137/625.47 |

FOREIGN PATENT DOCUMENTS

| | | |
|---|---|---|
| EP | 0345396 A1 | 12/1989 |
| WO | WO-03039646 A1 | 5/2003 |

OTHER PUBLICATIONS

European Search Report dated Feb. 12, 2004 (4 pages).

* cited by examiner

Primary Examiner—Nicholas D. Lucchesi
Assistant Examiner—Mark K. Han
(74) Attorney, Agent, or Firm—Miller Matthias & Hull (57) ABSTRACT

A fluid control apparatus is disclosed for controlling fluid flow between a catheter, an injector, a saline supply, a waste dump and a contrast supply. The apparatus includes a valve stem movable within a cavity disposed in a valve body. The valve stem is movable to a plurality of positions including a contrast position where the valve stem provides communication between the injector and a contrast supply, a saline/waste position where the valve stem provides communication between the injector and a saline/waste line and an injection position where the valve stem provides communication between the injector and an outlet port connected to the catheter.

25 Claims, 9 Drawing Sheets

ROTARY MANIFOLD SYRINGE

TECHNICAL FIELD

Fluid injection and aspiration apparatuses and, more particularly, angiographic fluid manifold syringes are disclosed.

BACKGROUND OF THE RELATED ART

Many medical procedures require the injection or aspiration of fluid. One example is angiography. Angiography is a procedure used in the detection and treatment of stenotic or narrowed blood vessels. During angiography, a radiographic image of a vascular structure is obtained by injecting radiopaque fluid or contrast through a catheter into a vein or artery. The contrast is injected into a patient using a syringe which is powered either manually or by a power injector. Throughout the procedure, the injection device and catheter remain in fluid communication with the vein or artery.

Once the contrast is injected into the targeted blood vessel, the vascular structure fills with contrast. X-rays are then taken of the region of the body in which the contrast material was injected which allow for visualization of the vessel containing contrast by creating a radiographic image of the blood vessel containing the contrast material. The radiographic image of the blood vessels filled with the contrast material is usually recorded onto film or videotape and then displayed on a fluoroscopic monitor.

During this procedure, it may also be necessary to inject the patient with saline solution or other fluids. Like the contrast, these fluids are injected into the patient using a syringe.

In addition to injecting fluids, the treating physician may also want to remove fluids from the patient for culture or other diagnostic procedures. Fluid is aspirated by drawing the fluid into a syringe and then pumping it out of the syringe into a collection receptacle either manually or by a powered pump.

Because many different fluids may be injected or aspirated with a syringe during angiography and other medical procedures, the syringe must be connected easily and quickly to several different fluid lines. As a result, the syringe is commonly attached to a multi-port manifold which has ports connected to many different fluid sources.

Currently, many devices for fluid management consist of a syringe adapted to be attached to a separate manifold having multiple handles, e.g. one to five, which are used to control the injection or aspiration of various fluids. While the manifold may have any number of control handles, most manifolds have three handles which are connected to a saline fluid line, a contrast fluid line and a fluid line connected to a pressure transducer. A fourth port is sometimes included for connection to a collection or waste receptacle. Control handles on each port of the multi-port manifold regulate the amount of fluid that enters or exits the syringe. Each handle may have a different routing configuration or degree of rotational freedom depending on the design of the manifold. For example, it is common for handles to have rotational positions of 90°, 180° or 270°.

It would be advantageous to have a smaller device that has one control handle and incorporates the functions of the syringe and the manifold. One advantage of using a smaller, single-handle manifold syringe is that the operator is able to quickly switch between operative ports. Additionally, the single-handle manifold syringe is easier to use because only one handle must be manipulated.

It would therefore be advantageous to provide a fluid management apparatus which performs the functions of a syringe and multi-port manifold for injection and aspiration of fluids and which has a single control handle to facilitate use of the device.

SUMMARY OF THE DISCLOSURE

In satisfaction of the aforenoted needs, a fluid control apparatus is disclosed for controlling fluid flow between a catheter, an injector, a saline supply, a waste dump or receptacle and a contrast supply. The apparatus comprises a body comprising a cavity, an outer surface and a plurality of ports providing communication between the cavity and the outer surface. The plurality of ports comprise at least one outlet port connected to the catheter, a contrast port connected to the contrast supply, a saline port connected to the saline supply and a waste port connected to the waste dump. The saline and waste ports may be combined as a single saline/waste port with appropriate one-way check valves providing the correct flow to and from the saline supply and waste dump. The body is connected to the injector to provide communication between the injector and the cavity.

The cavity accommodates a valve stem. The valve stem comprises a plurality of connecting passages extending through the valve stem and including a contrast passage, a saline passage, a waste passage and an injection passage that selectively provide communication between the cavity and the contrast port, the saline port, the waste port and the outlet port, respectively, depending upon a position of the valve stem. If the saline and waste ports of the body are combined as a single saline/waste port, the saline and waste passages of the valve stem may be combined as a single saline/waste passage.

The valve stem is movable within the cavity to at least four positions including a contrast position where the contrast passage of the valve stem provides communication between the cavity and the contrast port, a saline position with a saline passage provides communication between the cavity and the saline port, a waste position where the waste passage provides communication between the cavity and the waste port and an injection position where the injection passage provides communication between the cavity and the outlet port. If the saline and waste ports of the body are combined as a single saline/waste port and the saline and waste passages of the valve stem are combined as a single saline/waste passage, the valve stem needs to be movable to only three positions—contrast, saline/waste and injection. The body of the apparatus may also include a pressure transducer port which is connected to a pressure transducer. The valve stem may also be designed so that the pressure can be monitored while the valve stem is in one or more of the saline, contrast and waste positions but, preferably, the valve stem would isolate the pressure transducer while the valve stem is in the injection position.

While the disclosed fluid management apparatuses are susceptible to various modifications and alternative constructions, certain illustrative embodiments thereof have been shown in the drawings and will be described below in detail. It should be understood, however, that there is no intention to limit the disclosure to the specific apparatuses disclosed, but on the contrary, the disclosure is intended to cover all modifications, alternative constructions and equivalents falling within the spirit and scope of the appended claims.

DETAILED DESCRIPTION OF THE PRESENTLY PREFERRED EMBODIMENTS

Figure 1:
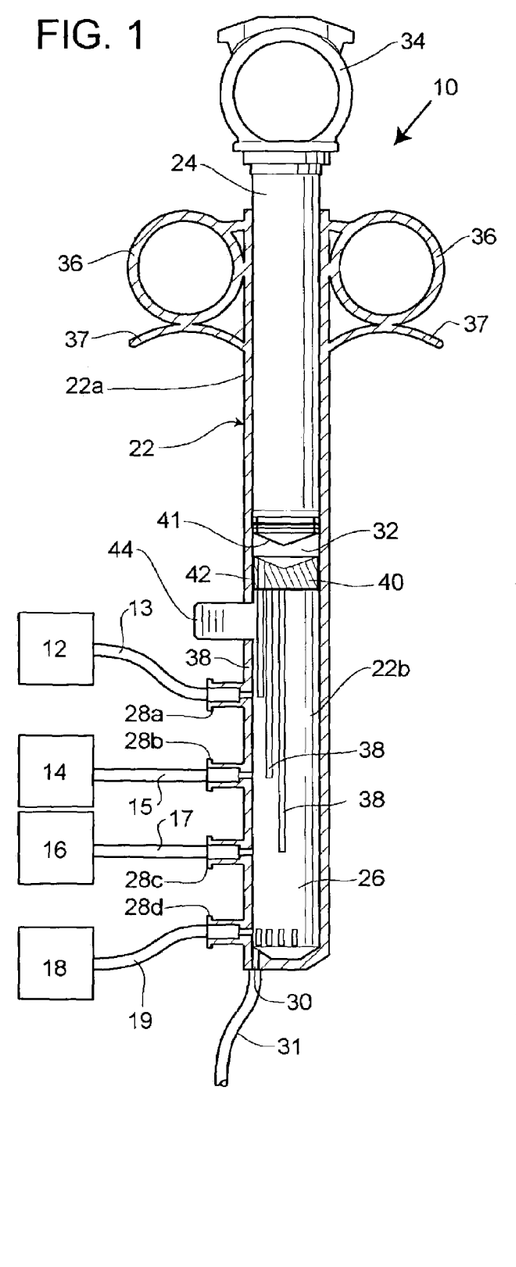
FIG. 1 is a front elevational view of a disclosed manual fluid management apparatus with portions of the outer cover removed.

Referring now to the drawings, and with specific reference to FIG. 1, a manually operated fluid management apparatus is generally depicted by reference numeral 10. While the apparatus 10 has use in many different medical procedures, it may be of particular use in a procedure known as angiography. In angiography it may be necessary to inject different fluids into a patient such as a radiopaque contrast from a contrast source 12 connected to the apparatus 10 by a fluid line 13 or saline solution from a saline source 14 connected to the apparatus 10 by a fluid line 15. It is to be understood that the apparatus 10 can be used for the injection of other fluids and in power-assisted, or automatic injection systems as well. Additionally, it may be necessary to remove or aspirate fluids from the patient to be deposited in a collection or waste receptacle 16. The collection receptacle 16 is connected to the apparatus 10 by a fluid line 17. The aspirated fluids are frequently used to perform other diagnostic procedures. Further, the apparatus 10 may also be connected to a pressure transducer 18 so that pressures, such as blood pressure and venous pressure, may be monitored during the medical procedure being performed. The pressure transducer 18 is connected to the apparatus 10 by a fluid line 19.

As illustrated in FIGS. 20–23, separate saline and waste ports are not required and a single combination saline/waste port may be provided that is linked to both a saline reservoir and a waste dump. Appropriate one-way check valves may then be employed to control the flow of fluid from the saline reservoir to the valve stem and to control the flow of waste fluid from the valve stem to the waste dump and not vice versa.

As shown in FIG. 1, the fluid management apparatus 10 includes a body 22, a plunger or injector 24, a rotary valve stem 26, a plurality of ports 28a, 28b, 28c and 28d and an aperture 30 that may be connected to a catheter 31. The body 22 includes a cavity 32 that is a temporary storage location for fluids passing into and out of the apparatus 10 during injection or aspiration.

The plunger 24 is housed in a proximal end 22a of the body 22 and is slidably connected to the inside walls of the body 22. On one of its ends, the plunger 24 has an extension 34 that extends outside the body 22. In a preferred embodiment, the plunger extension 34 is a circular-shaped which allows it to be easily gripped by an operator. When this extension 34 is gripped, the plunger 24 may be easily manipulated to partially withdraw the plunger 24 from the body 22 which creates a vacuum that draws fluids into the barrel cavity 32. The plunger 24 is then reinserted into the body 22 to force fluids out of the barrel cavity 32.

As shown in FIG. 1, the body 22, like the plunger 24, has circular-shaped extensions 36 that may be easily gripped by an operator when the apparatus 10 is in use. In an embodiment, two barrel extensions 36 extend from opposing sides of the body 22. Each of these extensions 36 has a curved flange 37 that assists the operator to firmly grasp and hold the body 22 during use of the apparatus 10. In alternate forms of the invention, there may be any number of extensions 36 on the body 22. The barrel extensions 36 and the plunger extension 34 are positioned on the apparatus 10 such that they may easily be grasped to operate the apparatus 10. This design is advantageous because it is easier to control than current, bulkier designs which are difficult to hold and operate simultaneously. Although the extensions on the plunger 24 and the body 22 are shown as circular-shaped, alternate forms of the invention may have extensions of a different shape.

Figure 2:
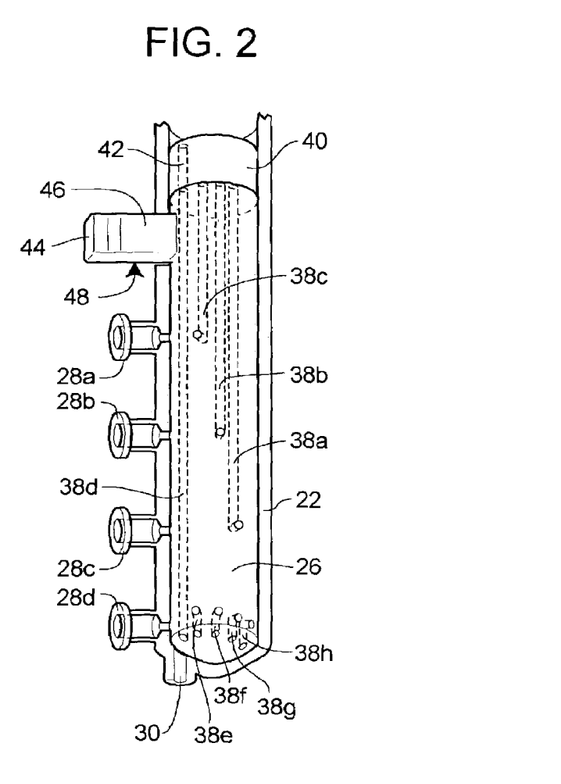
FIG. 2 is a perspective, fragmentary view of the fluid management apparatus of FIG. 1 with outer cover removed.
Figure 3:
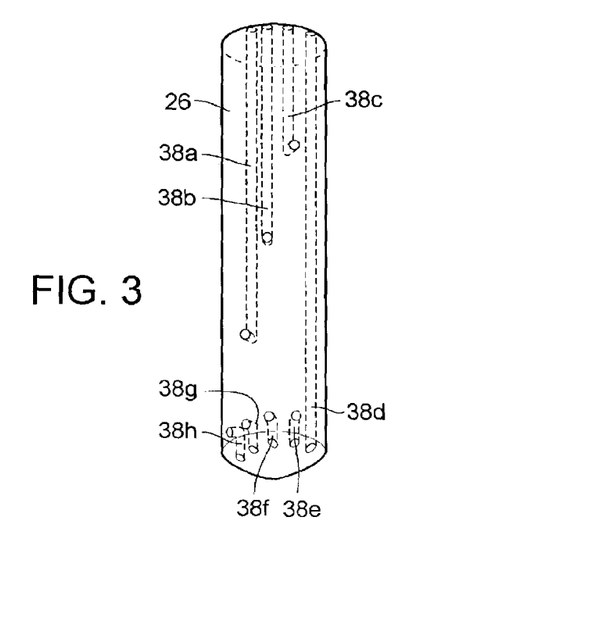
FIG. 3 is a perspective view of a valve stem of the fluid management device of FIG. 1.

The distal end 22b of the body 22 also houses the rotary valve stem 26. As illustrated in FIGS. 1–3, the valve stem 26 includes a plurality of passages 38a, 38b, 38c, 38d, 38e, 38f, 38g and 38h through which the fluids travel during injection and aspiration. These passages 38a–h, positioned circumferentially about the valve stem 26, maintain fluid communication between different structural elements of the apparatus 10 which enable the apparatus 10 to perform three of its primary functions: injection, aspiration and pressure measuring. To accomplish these functions, the cylinder passages 38a–h are positioned such that each channel 38a–h facilitates fluid communication between different pairs of structural elements. For example, as shown in FIGS. 1–3, some passages 38a–c assist to fluidically connect the ports 28a–c to the cavity 32, some of the passages 38e–h assist to fluidically connect one of the ports 28d to the aperture 30, and one of the passages 38d assists to fluidically connect the cavity 32 and the aperture 30.

With continued reference to FIG. 1, a separator 40 is positioned between the valve stem 26 and the cavity 32. The separator 40 has a channel 42 that is used to communicate fluids between the cylinder passages 38a–d and the cavity 32. In the embodiment shown in FIG. 1, the separator 40 has a substantially concave side that is geometrically configured to receive the end 41 of the plunger 24. The end 41 may also be conically shaped. Because the separator 40 has a single channel 42, the separator 40 controls or limits the passage of fluids between the cavity 32 and each cylinder channel 38a–d. The separator is also an important element of the apparatus 10 because it prevents the leakage of fluids from non-operative ports into the barrel cavity 32, thereby ensuring that the syringe and multi-port manifold operations can be combined to form this uni-modular apparatus 10. Such a uni-modular design is advantageous, inter alia, because the user does not have to disconnect and reconnect the syringe from a manifold, a common method by which damaging air bubbles are generated in conventional apparatuses.

Because only one cylinder channel 38a–d may be operative at a time, the valve stem 26 rotates so that each cylinder channel 38a–d may be moved into alignment with the separator channel 42. In a preferred embodiment, the valve stem 26 rotates such that each of the ports 28a–d is sequentially in fluid communication with the separator channel 42 and the cavity 32. The rotation of the valve stem 26 is controlled by a handle 44. The handle 44 is fixedly attached to the valve stem 26 and extends through an opening or slot (not shown) in the body 22. The handle 44 has two flat surfaces 46, 48 that may be gripped or pushed by an operator. By applying a force, the operator can move the handle into different positions thereby causing the valve stem 26 to rotate.

In an embodiment, the valve stem 26 is held in each desired rotational position by small ribs (not shown) which protrude from the outer surface of the valve stem 26 and lock into small detents (not shown) on the inside wall of the body 22. When the cylinder is not in a predetermined rotational position, the ribs do not line up with the dimples and thus can not help retain the cylinder in a desirable position. To rotate the valve stem 26 from one position to another, the operator applies a force in the desired direction moving the handle 44 and disengaging the ribs from detents. Because the ribs are made of a deformable material, they may be easily engaged, disengaged and re-engaged with the detents by an operator applying a small amount of force.

When the handle 44 is moved to the next desired position, the ribs and detents re-engage to prevent the cylinder from further rotation. Alternate embodiments may have a cylinder that is able to remain in each rotational position because of the interference fit between the cylinder and the barrel, thereby preventing the cylinder from rotating unless the handle is moved. Each rotational position of the handle 44 allows a different cylinder channel 38a–h to be either aligned with the cavity 32 or the aperture 30. These rotational positions will be discussed in more detail in connection with FIGS. 4–15 below.

In a preferred embodiment, as is shown in FIG. 1, the handle 44 is located near the end of the valve stem 26 that is adjacent the separator 40. This location is ergonomically better than current designs because it is easier for the operator to use the plunger extension 34 and the handle 44 during operation of the apparatus 10. In an alternate embodiment, the handle may be located in a different position along the barrel. Additionally, in other embodiments, the handle could be a button, a switch, a spring-based handle, or any other form of a control mechanism known by those skilled in the art.

Figure 4:
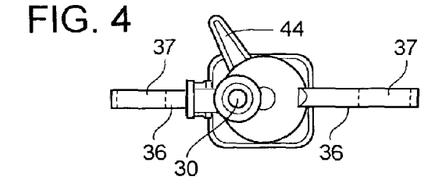
FIG. 4 is a bottom plan view of the fluid management apparatus having a control handle in a first position.
Figure 5:
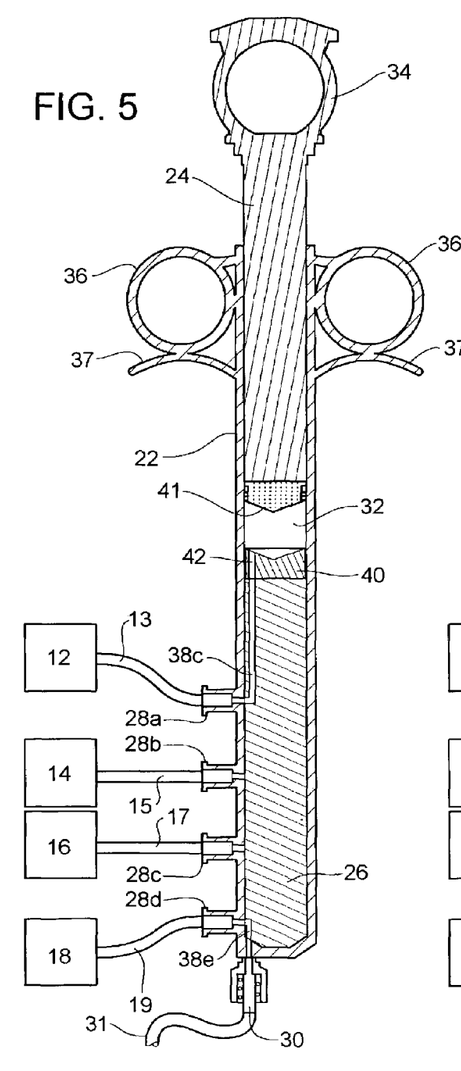
FIG. 5 is a sectional view of the fluid management apparatus with the valve stem in a first position when the control handle is in a first position as shown in FIG. 4.
Figure 6:
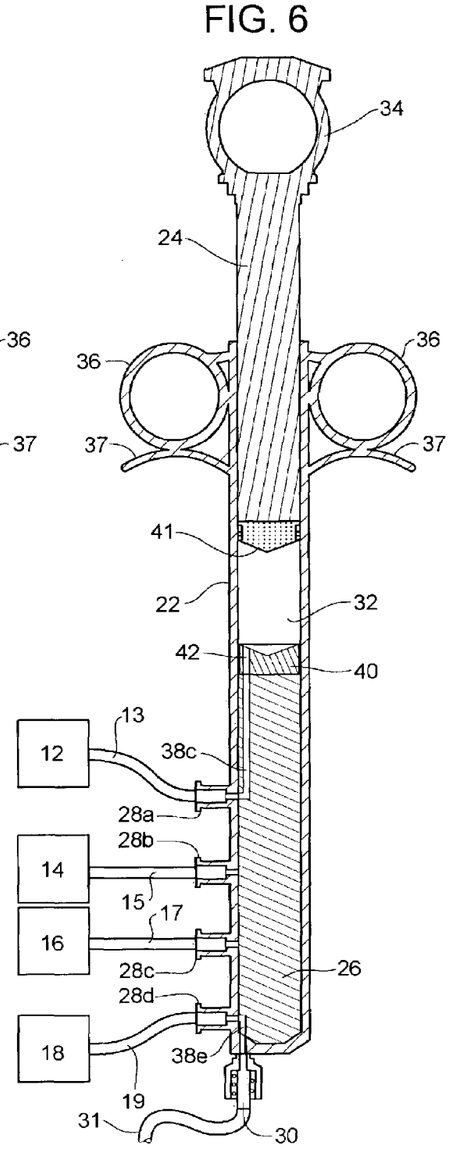
FIG. 6 is a sectional view of the fluid management apparatus with the valve stem in a first position as shown in FIG. 5 and a plunger partially withdrawn from the apparatus to draw fluid into the cavity of the apparatus.

FIGS. 4–15 show the preferred embodiment of the fluid management apparatus 10 which includes a valve stem 26 having five rotational positions. Specifically, FIGS. 4–9 illustrate the various positions of the valve stem 26 during injection. As shown in FIGS. 4–6, before injection of contrast, the contrast must be drawn from the source 12 of contrast into the apparatus 10. To accomplish this, the handle 44 is placed in a first position (FIG. 4) which corresponds to first rotational position of the valve stem 26. As shown in FIG. 5, when the handle 44 is in this first position, the valve stem 26 is positioned such that a cylinder channel 38c is aligned with the separator channel 42 and a cylinder channel 38e is aligned with the aperture 30. Before drawing contrast into the apparatus 10, the plunger 24 must be inserted almost completely into the body 22. Then, as shown in FIG. 6, the plunger 24 is partially withdrawn from the body 22 thereby creating a larger cavity 32 to receive and store the contrast before injection. As the plunger 24 is withdrawn from the body 22, a vacuum is created within the body 22 which draws the contrast from the contrast source 12 and sends contrast through the fluid line 13, port 28a, cylinder channel 38c and separator channel 42 until it reaches the barrel cavity 32 where it is stored until injection. As the contrast is drawn into the cavity 32, port 28d is in fluid communication with aperture 30 via cylinder channel 38e.

In the embodiment shown in FIGS. 5 and 6, port 28d is a pressure port connected to a pressure transducer 18. Because port 28d is in fluid communication with fluid in the catheter 31 attached to the aperture 30, the pressure transducer 18 is able to measure pressures in the body such as blood pressure and venous pressure. This ability to measure pressures while fluids are drawn into a syringe for injection purposes is advantageous, inter alia, because the physicians can continually monitor the patient for sudden changes in pressure which may be problematic for the procedure being performed. Current fluid management devices are not generally designed to allow pressure measurement in this manner. Additionally, the design of the apparatus is advantageous because the transducer, which has its own cylinder channel 38e, cannot be damaged by the forces created during injection and aspiration.

Figure 7:
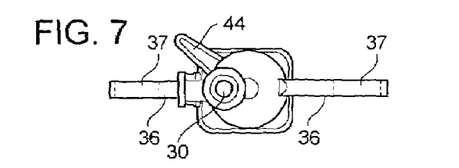
FIG. 7 is a bottom plan view of the fluid management apparatus having the control handle in a second position.
Figure 8:
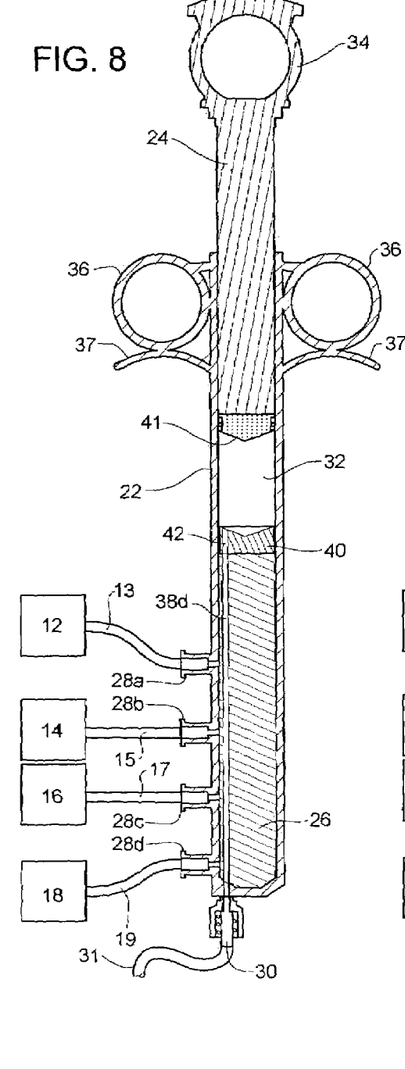
FIG. 8 is a sectional view of the fluid management apparatus with the valve stem in a second position when the control handle is in a second position as shown in FIG. 7 and the plunger partially withdrawn from the apparatus.
Figure 9:
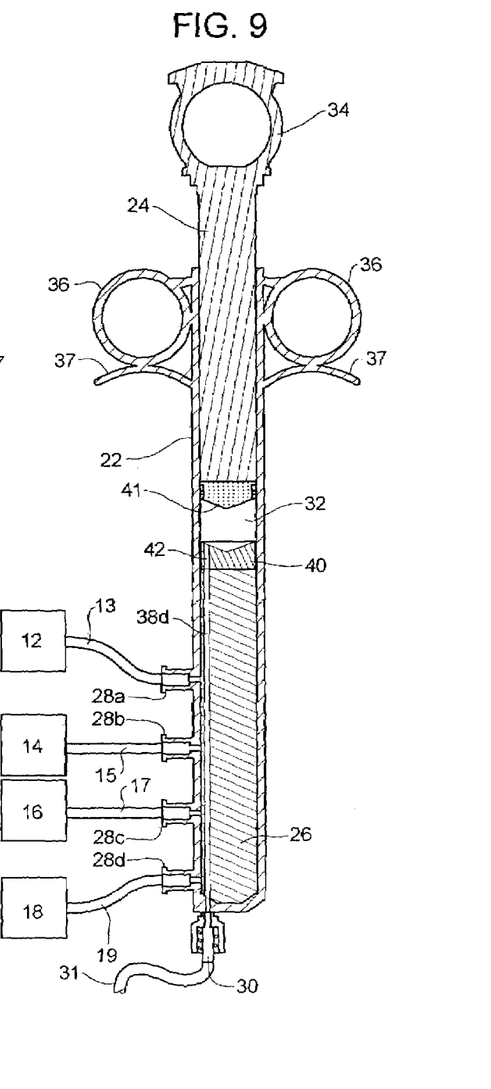
FIG. 9 is a sectional view of the fluid management apparatus with the valve stem in a second position as shown in FIG. 8 and the plunger inserted into the apparatus to force fluid out of the apparatus.

Referring now to FIGS. 7–9, to complete the injection process, the contrast must be forced out of the apparatus 10. To accomplish this, the contrast is held in the cavity 32 while the handle 44 is rotated to a second position. FIG. 7 shows the handle 44 in a second position which corresponds to a second rotational position of the valve stem 26. FIG. 8 shows the second rotation position of the valve stem 26 which corresponds to the second position of the handle 44. The valve stem 26 is positioned such that a cylinder channel 38d is aligned with both the separator channel 42 and the aperture 30. When the plunger is reinserted into the body 22, as shown in FIG. 9, the contrast is forced out of the cavity 32, through the separator channel 42 and the cylinder channel 38d, out of the aperture 30 and, finally, into the catheter 31. During procedures such as angiography, the aperture 30 is connected to the catheter 31 which allows the contrast to flow through the catheter 31 to the target blood vessel. In alternate forms of the invention a needle or other medical device may be attached to the aperture 30 instead of the catheter 31. As is shown in FIGS. 8 and 9, when fluid is injected into a patient, the pressure port 28d is no longer connected by cylinder passages to the aperture 30. Because pressure port 28d is closed off during injection, the pressure transducer is not damaged by the forces of injection.

Figure 10:
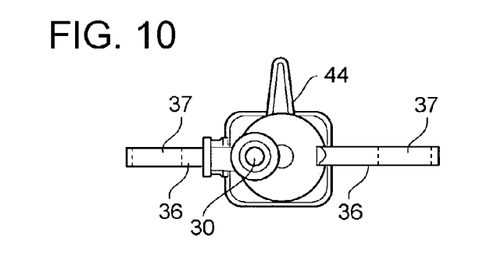
FIG. 10 is a bottom plan view of the fluid management apparatus having the control handle in a third position.
Figure 11:
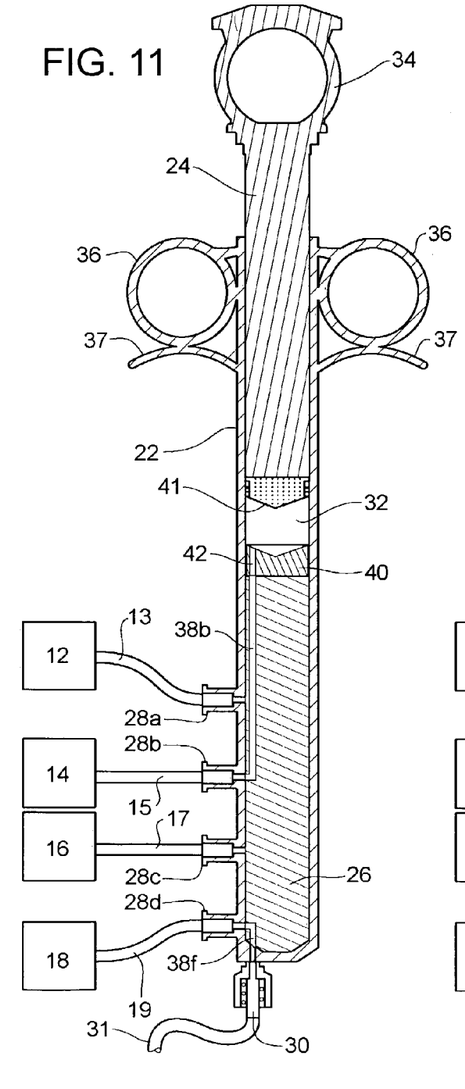
FIG. 11 is a sectional view of the fluid management apparatus with the valve stem in the third position when the control handle is in the third position as shown in FIG. 10.

FIGS. 10 and 11 show the positions of the handle 44 and the valve stem 26 when the saline port 28b is operational for purposes of bringing saline from the saline source 14 into the cavity 32 prior to injection. FIG. 10 illustrates a third operative position of the handle 44. FIG. 11 shows a third rotational position of the valve stem 26 which corresponds to the third position of the handle 44. First, the cylinder is rotated to align a cylinder channel 38b with the separator channel 42. Then saline may be drawn into the cavity 32 and injected into the patient using the same procedures as discussed and depicted in connection with the injection of contrast (FIGS. 4–9). This third position of the valve stem 26, like the first position of the valve stem 26, has a cylinder channel 38f that connects the pressure port 28d to the aperture 30 so that the blood pressure in the catheter, or other medical device, may be monitored while saline is drawn into the cavity 32.

Figure 12:
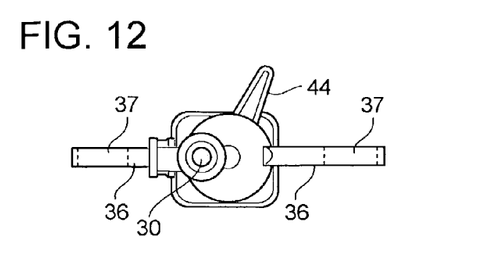
FIG. 12 is a bottom plan view of the fluid management apparatus having the control handle in a fourth position.
Figure 13:
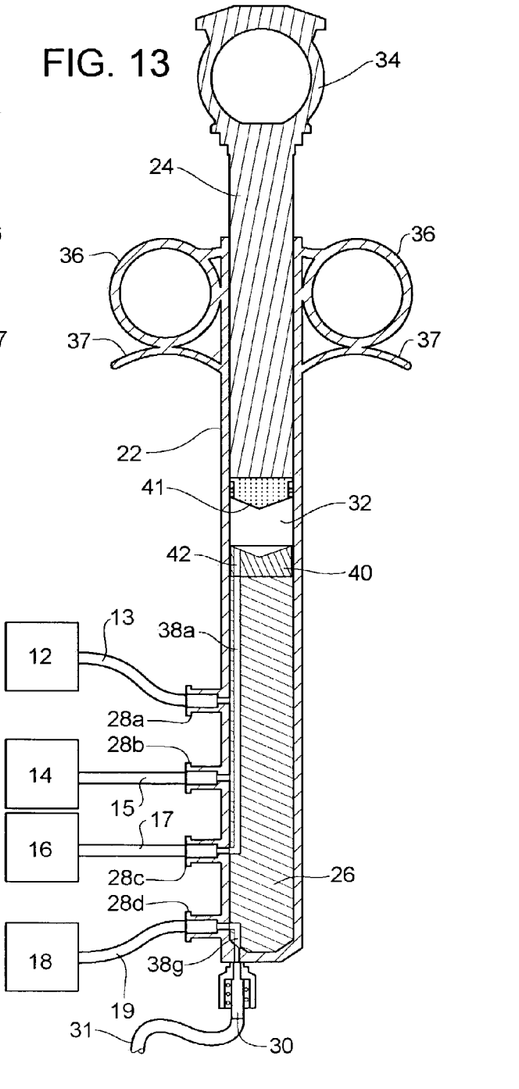
FIG. 13 is a sectional view of the fluid management apparatus with the valve stem in a fourth position when the control handle is in the fourth position as shown in FIG. 12.

FIGS. 12 and 13 show the positions of the handle 44 and the valve stem 26 when port 28c is operational for releasing waste produce from the patient or contaminated saline and/or contrast fluid. FIG. 13 shows the fourth rotational position of the valve stem 26 which corresponds to the fourth position of the handle 44. As will be discussed next, the process of aspiration is essentially the reverse of injection.

To aspirate fluids, the valve stem 26 is first rotated into its second position as illustrated in FIG. 9. Then, as shown in FIG. 8, fluid is drawn into the cavity 32 by the vacuum created in the cavity 32 when the plunger 24 is partially withdrawn from the body 22. The aspirated fluid is temporarily stored in the cavity 32 as the valve stem 26 is rotated to the fourth position. As illustrated in FIG. 13, the fourth position of the valve stem 26 aligns a cylinder channel 38a with the separator channel 42. Additionally, FIG. 13 shows the plunger 24 in a position after it has been reinserted into the body 22. During aspiration, the plunger 24 forces the fluid out of the cavity 32, through the separator channel 42, the cylinder channel 38a and port 28c, and into collection receptacle 16. This fourth position of the valve stem 26, like the first and third positions of the valve stem 26, has a cylinder channel 38g that connects the pressure port 28d to the aperture 30 so that the blood pressure in the catheter, or other medical device, may be monitored while fluid is ejected from the cavity 32 and into the collection receptacle 16.

Figure 14:
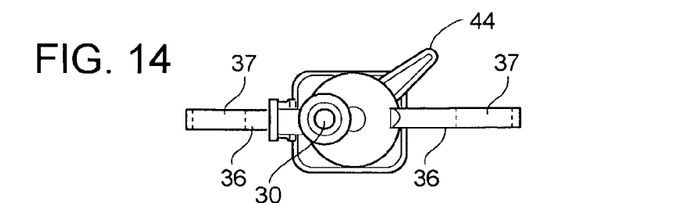
FIG. 14 is a bottom plan view of the fluid management apparatus having the control handle in a fifth position.
Figure 15:
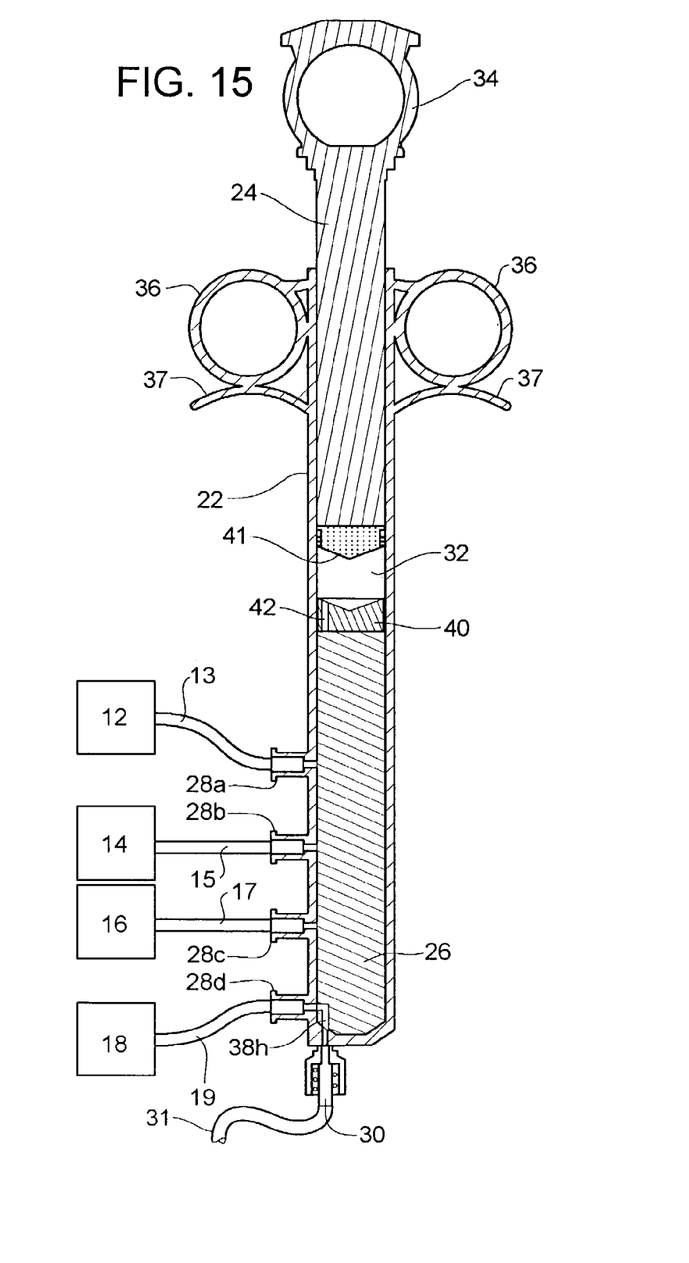
FIG. 15 is a sectional view of the fluid management apparatus with the valve stem in a fifth position when the control handle is in the fifth position as shown in FIG. 14.

In addition to injecting and aspirating fluids, the apparatus 10 may be used solely to measure fluid pressures in the catheter 31. As shown in FIG. 14, the handle 44 may be moved into a fifth operative position to operate only the pressure port 28d. FIG. 15 shows the fifth rotational position of the valve stem 26 which corresponds to the fifth position of the handle 44. In this fifth position of the preferred embodiment, a cylinder channel 38h connects pressure port 28d with the aperture 30. As discussed, if a catheter 31 is attached to the aperture 30, the pressure transducer which is connected to the pressure port 28d may then be used to measure and monitor the fluids in the catheter 31.

Figures 16, 17:
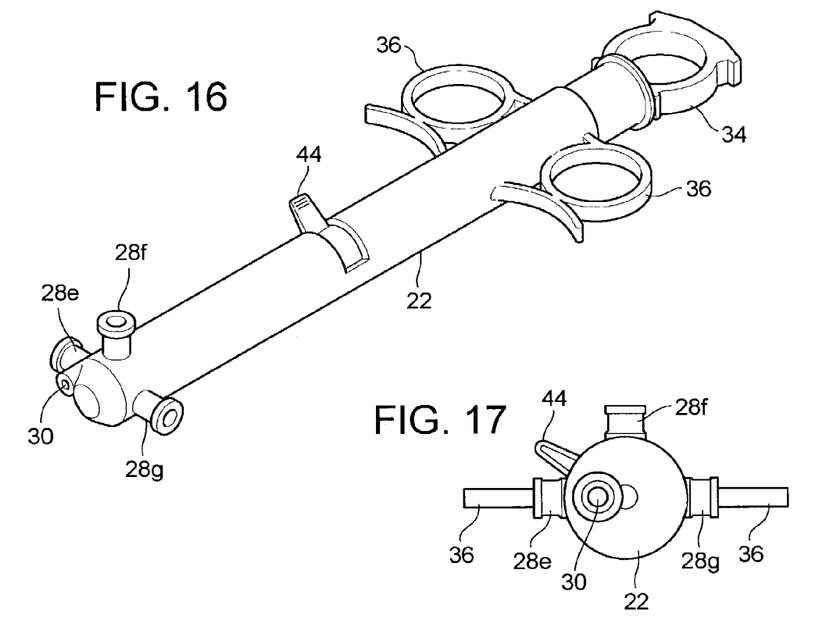
FIG. 16 is an isometric view of a fluid management apparatus having a plurality of ports in a radial configuration around a barrel of the apparatus.
FIG. 17 is a bottom plan view of the fluid management apparatus of FIG. 16.
Figures 18, 19:
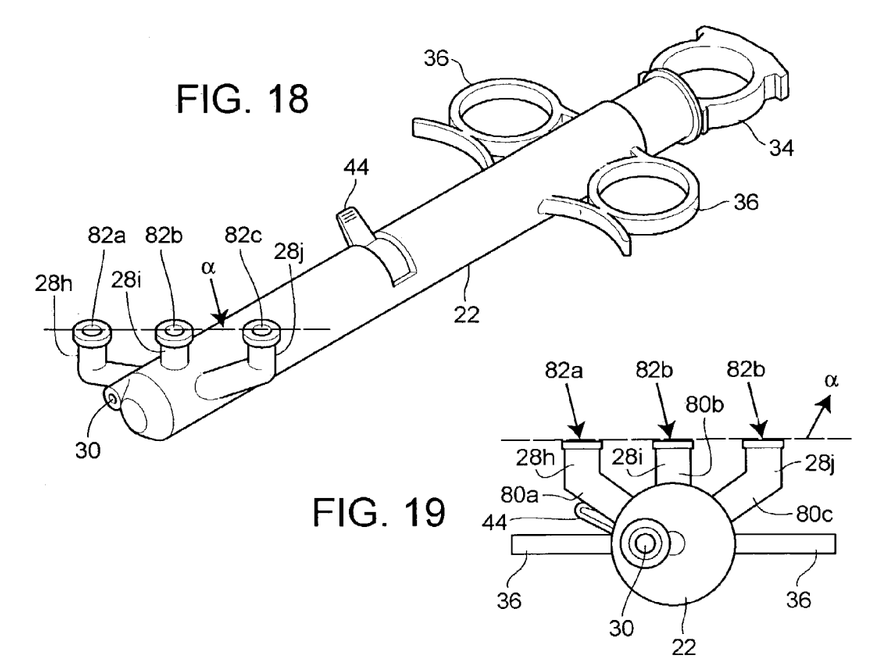
FIG. 18 is an isometric view of a fluid management apparatus having a plurality of ports in a radial configuration and wherein each port includes an extension arm.
FIG. 19 is a bottom plan view of the fluid management apparatus of FIG. 18.
Figure 20:
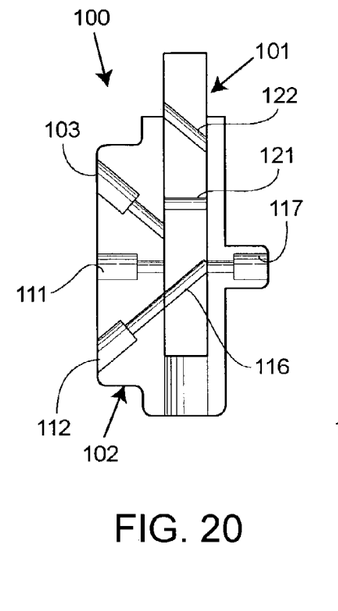
FIG. 20 is a schematic sectional view of a fluid management apparatus incorporating a sliding valve stem with the valve stem in a first position.

Referring back to FIG. 1, the plurality of ports 28a–d are positioned on the outside of the body 22 in a line which is parallel to the axis (not shown) of the body 22. In this configuration the cylinder passages 38a–h associated with each port 28a–d, vary in length. In alternate embodiments, as shown in FIGS. 16 and 17, the ports 28e, 28f and 28g may be positioned radially about the body 22. In a radial configuration, the ports 28e–g may be spaced circumferentially around the outside of the body 22 such that the ports 28e–g are associated with cylinder passages (not shown) that are the same length. However, in the radial configuration, the ports may also be in a helical configuration such that the ports are associated with cylinder passages of varying lengths. Still further, in alternate embodiments as shown in FIGS. 18 and 19, the ports 28h, 28i, and 28j may each have an arm 80a, 80b and 80c. The arms 80a–c extend the ports away from the body 22 such that the opening 82a–c of each port 28h–j is in the same plane as illustrated by dashed line α. This configuration is advantageous because each of the fluid lines attached to the apparatus 10 for injection, aspiration, pressure measurement or any other desired function, is less likely to become tangled with another fluid line. In yet other forms of the invention, the ports may be positioned in another configuration so long as the cylinder passages are able to perform the same functions as discussed in connection with FIGS. 1–15 above.

In another alternate embodiment of the apparatus 10, the separator may be rotatable. In this embodiment, the cylinder remains fixed within the barrel. The cylinder passages may become operative by rotating the separator which would the separator channel with the various cylinder passages. Additionally, in this embodiment, the handle would be fixed to the separator rather than the cylinder.

Figure 23:
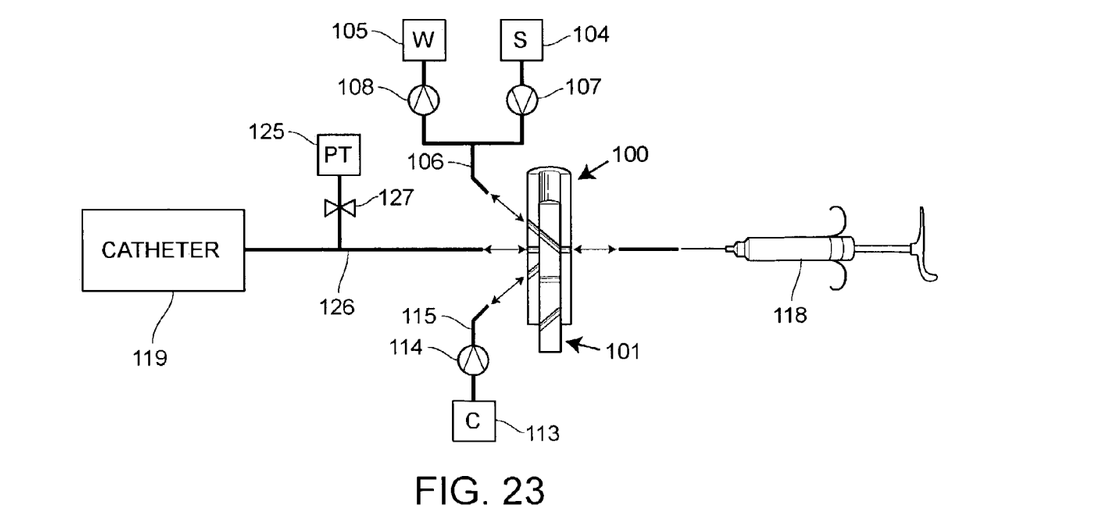
FIG. 23 is a schematic illustration of the fluid management apparatus of FIGS. 20–22 incorporated into an overall system with an injector, waste reservoir, saline and contrast supplies, pressure transducer and catheter.
Figure 24:
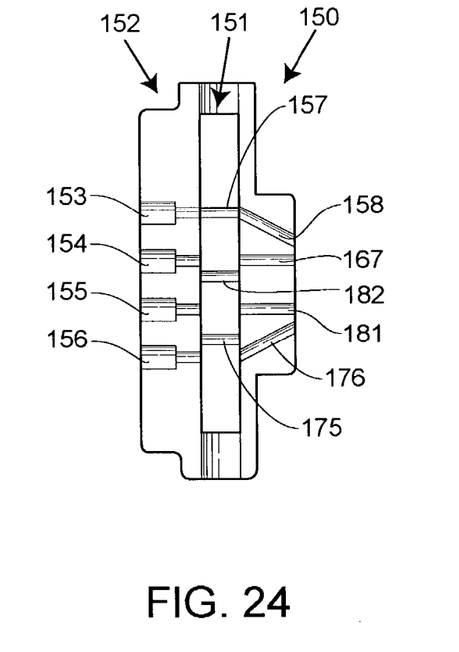
FIG. 24 is a sectional schematic view of another fluid management apparatus with a sliding valve stem in a first position.
Figure 25:
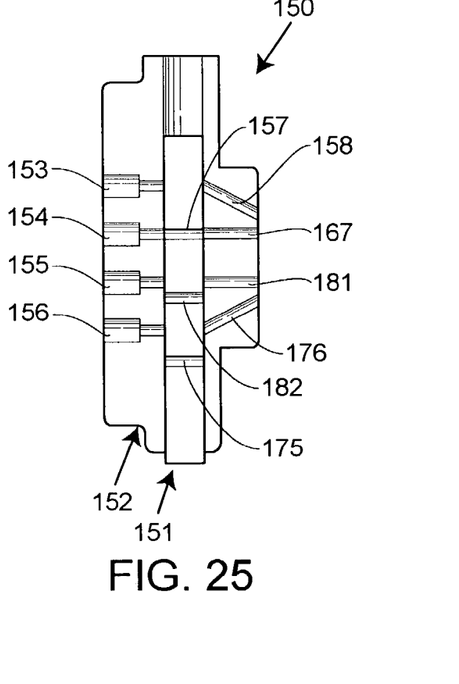
FIG. 25 is another schematic sectional view of the fluid management apparatus of FIG. 24 in a second position.

Referring to FIGS. 20–24, an alternative fluid management apparatus 100 is illustrated whereby the valve stem 101 is slidably received in the valve body 102. The valve body 102 includes a port 103 that, as illustrated in FIG. 23, is in communication with both a saline reservoir 104 and a waste dump 105. The common line 106 is connected to a one-way check valve 107 which permits fluid to be drawn from the saline reservoir 104 but not deposited back into the saline reservoir 104. Further, the common line 106 is also connected-to the waste dump 105 and a one-way check valve 108 is employed to permit flow from the valve stem 101 to the waste dump 105 and not vice versa. Alternatives to the one-way check valves 107, 108 can be employed, including mechanically operated pinch valves or other mechanical valves.

Returning to FIG. 20, in addition to the saline/waste port 103, the valve body 102 also includes an output port 111 and contrast port 112. The ports 103, 111 and 112 can be assigned any one of the three functions—contrast, saline/waste and output. Thus, assuming the port 112 is the contrast port 112, the sliding valve stem 101 is in the contrast position in FIG. 20 thereby providing communication between the contrast reservoir 113 (see FIG. 23) and the valve stem 101. An additional one-way check valve 114 can be employed to permit flow from the contrast reservoir 113 to the valve stem 101 and vice versa. Obviously, alternatives to the one-way check valve 114 including pinch valves or other mechanical isolation valves can be employed. Thus, in the position shown in FIG. 20, contrast may be drawn from the reservoir 113, through the line 115, through the port 112, through the contrast passage 116 of the valve stem 101 (see FIG. 20) and through the injector port 117 which is connected to the injector 118 (see FIG. 23). To inject contrast from the injector 118 to the catheter 119, the valve stem 101 is moved to the position shown in FIG. 21. Specifically, the injection passage 121 is aligned with the injection port 117 and outlet port 111 thereby providing communication between the injector 118 and catheter 119.

Figures 21, 22:
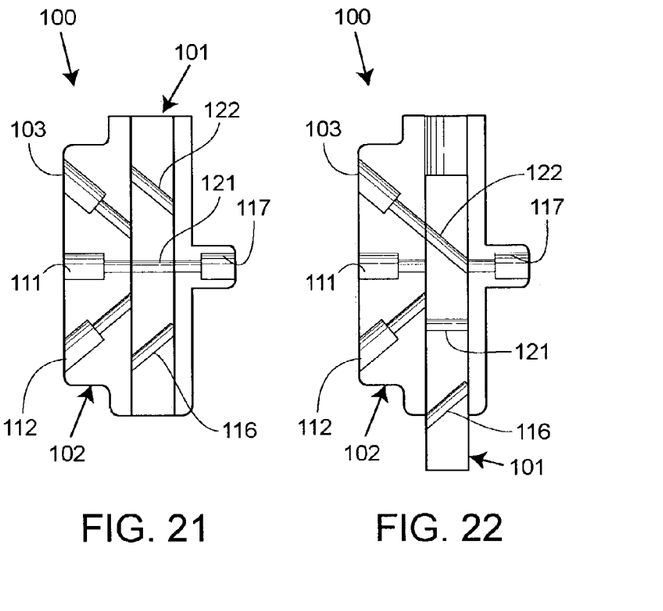
FIG. 21 is another sectional schematic view of the fluid management apparatus of FIG. 20 with the valve stem in a second position.
FIG. 22 is another sectional schematic view of the fluid management apparatus of FIG. 20 with the valve stem in a third position.

To either draw saline from the saline reservoir 104 or to inject waste into the waste dump 105, the valve stem 101 is then moved to the position shown in FIG. 22. Specifically, the saline/waste passage 122 is aligned with the injector port 117 and the saline/waste port 103 thereby providing communication between the injector 118 and the common line 106. In the position shown in FIG. 22, saline may be drawn from the saline reservoir 104, through the one-way check valve 107, into the common line 106, through the saline/waste passage 102, and into the injector 118. Once the saline is received in the injector 118, the valve stem 101 is then moved to the position shown in FIG. 21 so that the saline may be injected from the injector 118 to the catheter 119.

In contrast, to eject waste from the injector 118 to the waste dump 105, the valve stem is moved to the position as shown in FIG. 22 and the waste material is passed from the injector 118, through the injection port 117, through the passage 122, through the outlet 103, through the common line 108, through the one-way check valve 108 and into the waste dump 105.

In addition, a pressure transducer 125 may be connected to the catheter line 126. A valve 127 should be disposed between the pressure transducer 125 and the catheter line 126 so that the pressure transducer 125 can be protected from high pressure injection situations or those situations where by the valve stem 101 is in the position shown in FIG. 21. The valve 127 may be a pinch valve, isolation valve or other type of valve to isolate the pressure transducer in such high pressure situations.

Figure 28:
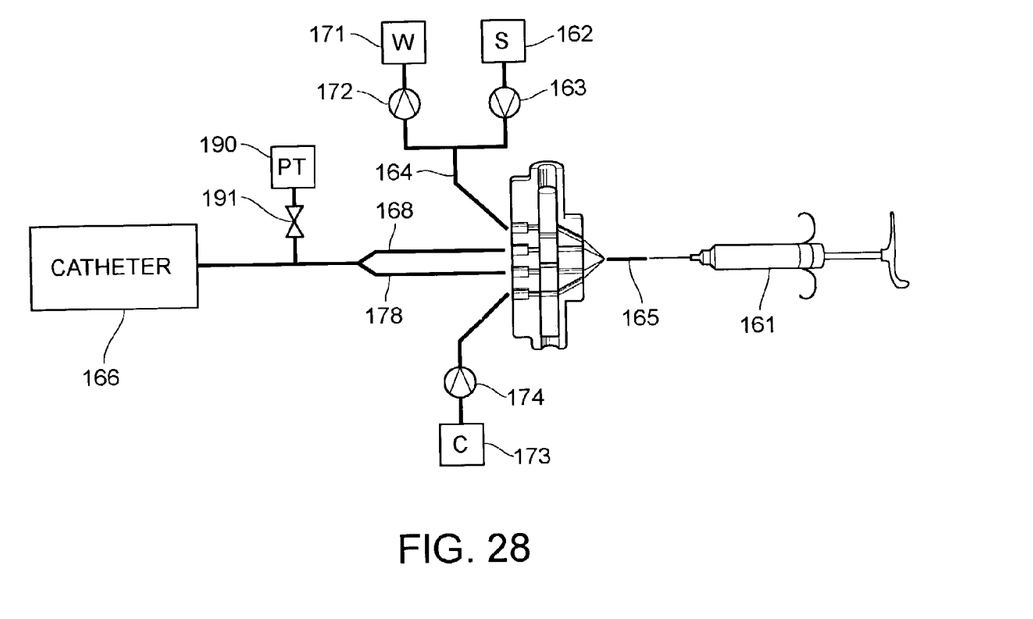
FIG. 28 is a schematic illustration of the fluid management apparatus of FIGS. 24–27 incorporated into an overall system with a waste reservoir, saline and contrast supplies, pressure transducer, catheter and injector.

Turning to FIGS. 24–28, an additional fluid control apparatus 150 is disclosed that includes a sliding valve stem 151 disposed within a valve body 152. The valve 152 includes a saline/waste port 153, a saline output port 154, a contrast output port 155, and a contrast port 156. In the position shown in FIG. 24, the valve stem 151 is moved into a position so that the saline/waste passage 157 is providing communication between the saline/waste port 153 and the passage 158 which is in communication with the injector 161 as shown in FIG. 28. Thus, in the position shown in FIG. 24, saline may be drawn from the saline reservoir 162, through the one-way check valve 163, through the common line 164, through the saline/waste port 153, through the saline/waste passage 157, through the passage 158, through the injector line 165 and into the injector 161. To inject the saline from the injector 161 to the catheter 166, the valve stem 151 is moved to the position shown in FIG. 25. In this position, the passage 157 provides communication between the passage 167 and the port 154. The port 154 is in communication with the saline line 168 which, in turn, is in communication with the catheter 166. To eject excess material, such as waste material, from the injector 161 to the waste reservoir 171, the valve stem is moved to the position shown in FIG. 24 where the waste material would pass through the passage 158, through the passage 157, through the port 153, through the common line 164 and through the one-way check valve 172 and into the waste dump 171.

Figure 26:
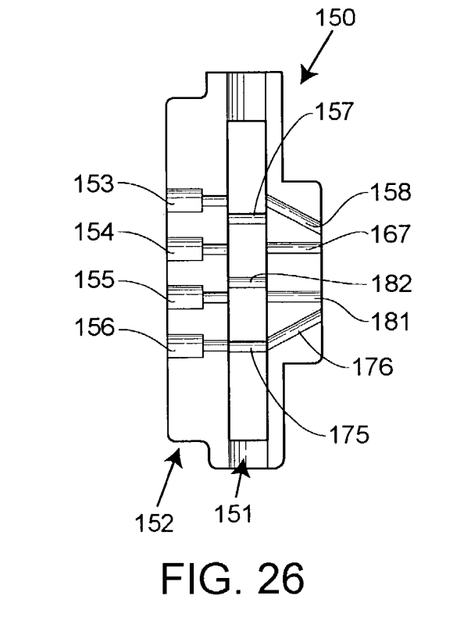
FIG. 26 is another sectional schematic view of the fluid management apparatus of FIG. 24 with the valve stem in a third position.
Figure 27:
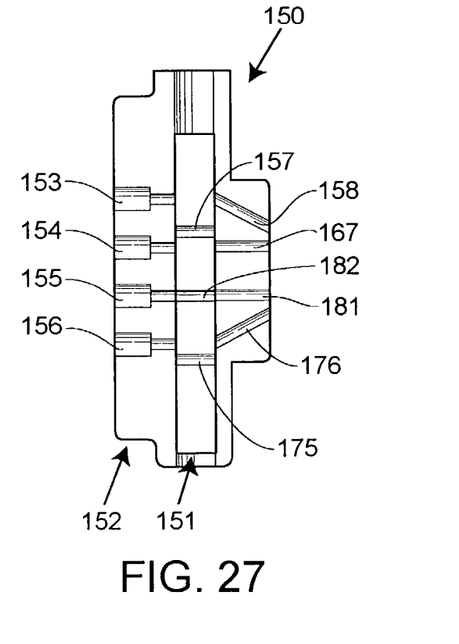
FIG. 27 is another sectional schematic view of the fluid management apparatus of FIG. 24 with the valve stem in a fourth position.

To draw contrast from the contrast reservoir 173 to the injector 161, the valve stem 151 is moved to the position shown in FIG. 26. Specifically, contrast may drawn from the contrast reservoir 173, through the one-way check valve 174, through the contrast port 156, through the contrast passage 175, through the passage 176, through the line 165 to the injector 161. To inject contrast from the injector 161 to the catheter 166, the valve 151 is moved to the position shown in FIG. 27 which is in communication with the separate contrast line 178. Contrast may be then ejected from the injector 161, through the line 165, through the passage 181, through the passage 182 and out the outlet port 155 which is connected to the contrast line 178. Using a separate saline/waste line 168 and a separate contrast line 178 may prove beneficial so as to keep contrast out of the saline line 168 and to keep saline out of the contrast line 178. Again, a pressure transducer 190 may be provided with a protecting valve 191 as discussed above with respect to FIG. 23.

The present invention has been described in terms of several preferred embodiments, each of which are intended to illustrate the principles of the present invention. One of ordinary skill in the art will appreciate that invention may be otherwise embodied without departing from the scope and spirit of the invention set forth in the appended claims.

What is claimed is:

1. A fluid control apparatus for controlling fluid flow between a catheter, an injector, a saline supply, a waste dump, and a contrast supply, the apparatus comprising:

a body comprising a cavity, an outer surface and a plurality of ports providing communication between the cavity and the outer surface, the plurality of ports comprising at least one outlet port connected to the catheter, a contrast port connected to the contrast supply, at least one saline/waste port connected to the saline supply and the waste dump, the body being connected to the injector to provide communication between the injector and the cavity, the cavity accommodating a valve stem, the valve stem comprising a plurality of connecting passages extending through the valve stem including a contrast passage, a saline/waste passage and an injection passage that selectively provide communication between the cavity and the contrast port, the saline/waste port and the outlet port respectively depending upon a position of the valve stem, the valve stem being movable within the cavity to at least three positions including a contrast position where the contrast passage of the valve stem provides communication between the cavity and the contrast port, a saline/waste position where the saline/waste passage provides communication between the cavity and the saline/waste port and an injection position where the injection passage provides communication between the cavity and the outlet port.

2. The fluid control apparatus of claim 1 wherein in the contrast position, the contrast passage provides communication between the contrast port and the cavity and the valve stem isolates the saline/waste and outlet ports.

3. The fluid control apparatus of claim 1 wherein in the saline/waste position, the saline/waste passage provides communication between the cavity and the saline/waste port and the valve stem isolates the contrast and outlet ports.

4. The fluid control apparatus of claim 1 wherein in the injection position, the injection passage provides communication between the cavity and the outlet port and the valve stem isolates the contrast and saline/waste ports.

5. The fluid control apparatus of claim 1 wherein the body further comprises a pressure transducer port providing communication between the cavity and the outer surface, the valve stem further comprises a pressure transducer passage extending through the valve stem and selectively providing communication between the pressure transducer port and the outlet port, and
    in the contrast position, the pressure transducer passage provides communication between the pressure transducer port and the outlet port.

6. The fluid control apparatus of claim 1 wherein the body further comprises a pressure transducer port providing communication between the cavity and the outer surface, the valve stem further comprises a pressure transducer passage extending through the valve stem and selectively providing communication between the pressure transducer port and the outlet port, and
    in the saline/waste position, the second pressure transducer passage provides communication between the pressure transducer port and the outlet port.

7. The fluid control apparatus of claim 1 wherein the body further comprises a pressure transducer port providing communication between the cavity and the outer surface, the valve stem further comprises a pressure transducer passage extending through the valve stem and selectively providing communication between the pressure transducer port and the outlet port, and
    in the injection position, the valve stem isolating the pressure transducer port from the outlet port.

8. The fluid control apparatus of claim 1 wherein the body further comprises a pressure transducer port providing communication between the cavity and the outer surface, the valve stem further comprises first and second pressure transducer passages that extend through the valve stem and selectively provide communication between the pressure transducer port and the outlet port, and
    in the contrast position, the first pressure transducer passage provides communication between the pressure transducer port and the outlet port,
    in the saline/waste position, the second pressure transducer passage provides communication between the pressure transducer port and the outlet port, and
    in the injection position, the valve stem isolating the pressure transducer port from the outlet port.

9. The fluid control apparatus of claim 8 wherein the valve stem further comprises a third pressure transducer passage extending through the valve stem and selectively providing communication between the pressure transducer port and the outlet port,
    the valve stem further being movable to a pressure reading position where the valve stem isolates the contrast and saline/waste ports and where the third pressure transducer passage provides communication between the pressure transducer port and the outlet port.

10. The fluid control apparatus of claim 1 wherein the body further comprises a pressure transducer port providing communication between the cavity and the outer surface,
    the valve stem further comprises a pressure transducer passage extending through the valve stem and selectively providing communication between the pressure transducer port and the outlet port,
    the valve stem further being movable to a pressure reading position where the valve stem isolates the contrast and saline/waste ports and where the pressure transducer passage provides communication between the pressure transducer port and the outlet port.

11. The fluid control apparatus of claim 1 wherein the valve stem is rotatably accommodated within the distal region of the cavity.

12. The fluid control apparatus of claim 1 wherein the valve stem is slidably accommodated within the distal region of the cavity.

13. The fluid control apparatus of claim 1 wherein the injector is a syringe.

14. The fluid control apparatus of claim 1 wherein the injector is a pump.

15. The fluid control apparatus of claim 1 wherein the saline/waste port comprises a separate saline port connected to the saline supply and a separate waste port connected to the waste dump, the saline/waste passage of the valve stem further comprises a separate saline passage and a separate waste passage, the valve stem being movable within the cavity to at least four positions including the contrast position where the contrast passage of the valve stem provides communication between the cavity and the contrast port, a saline position where the saline passage provides communication between the cavity and the saline port, a waste position where the waste passage provides communication between the cavity and the waste port and the injection position where by the injection passage provides communication between the cavity and the outlet port.

16. The fluid control apparatus of claim 15 wherein
    in the saline position, the saline passage provides communication between the cavity and the saline port and the valve stem isolates the contrast, waste and outlet ports.

17. The fluid control apparatus of claim 15 wherein
    in the waste position, the waste passage provides communication between the cavity and the waste port and the valve stem isolates the contrast, saline and outlet ports.

18. The fluid control apparatus of claim 15 wherein the body further comprises a pressure transducer port providing communication between the cavity and the outer surface, the valve stem further comprises a pressure transducer passage extending through the valve stem and selectively providing communication between the pressure transducer port and the outlet port, and
    in the saline position, the pressure transducer passage provides communication between the pressure transducer port and the outlet port.

19. The fluid control apparatus of claim 15 wherein the body further comprises a pressure transducer port providing communication between the cavity and the outer surface, the valve stem further comprises a pressure transducer passage extending through the valve stem and selectively providing communication between the pressure transducer port and the outlet port, and
 in the waste position, the pressure transducer passage provides communication between the pressure transducer port and the outlet port.

20. A fluid control valve for controlling fluid flow between a catheter, a saline supply, a waste dump, a contrast supply, a pressure transducer and an injector, the control valve comprising:
 a valve means movable to a plurality of positions including a contrast position where the valve means provides communication between the injector and the contrast supply while isolating the saline supply, waste dump, catheter, and pressure transducer,
 a saline position where the valve means provides communication between the injector and the saline supply while isolating the contrast supply, waste dump, catheter, and pressure transducer,
 a waste position where the valve means provides communication between the injector and the waste dump while isolating the contrast supply, saline supply, catheter, and pressure transducer,
 an injection position where the valve means provides communication between the injector and the catheter while isolating the contrast supply, saline supply and waste dump,
 wherein the valve means also maintains communication between the catheter and the pressure transducer in at least one of the contrast and saline positions.

21. A fluid control valve for controlling fluid flow between a catheter, a saline supply, a waste dump, a contrast supply, a pressure transducer and an injector, the control valve comprising:
 a valve means movable to a plurality of positions including
 a contrast position where the valve means provides communication between the injector the contrast supply while isolating the saline supply, waste dump, catheter and pressure transducer from the injector but providing communication between the catheter and the pressure transducer,
 a saline position where the valve means provides communication between the injector and the saline supply while isolating the contrast supply, waste dump, catheter and pressure transducer from the injector but providing communication between the catheter and the pressure transducer;
 a waste position where the valve means provides communication between the injector and the waste dump while isolating the contrast supply, saline supply, catheter and pressure transducer from the injector but providing communication between the catheter and the pressure transducer; and
 an injection position where the valve means provides communication between the injector and the catheter while isolating the pressure transducer, contrast supply and waste dump.

22. A fluid control apparatus for controlling fluid flow between a catheter, a saline supply, a waste dump, and a contrast supply, the apparatus comprising:
 a body comprising an open proximal end, a closed distal end, a cavity and an outer surface,
 the cavity comprising a proximal region for accommodating a plunger and a distal region for accommodating a valve stem,
 the distal end of the body comprising a plurality of ports providing communication between the cavity and the outer surface, the plurality of ports comprising at least one outlet port connected to the catheter, a contrast port connected to the contrast supply, a saline port connected to the saline supply, and a waste port connected to the waste dump,
 the valve stem comprising a plurality of connecting passages extending through the valve stem including a contrast passage, a saline passage, a waste passage and an injection passage that selectively provide communication between the proximal region of the cavity and the contrast port, the saline port, the waste port and the outlet port respectively depending upon a position of the valve stem,
 the valve stem being movable within the cavity to a plurality of positions including a contrast position where the contrast passage of the valve stem provides communication between the proximal region of the cavity and the contrast port, a saline position where the saline passage provides communication between the proximal region of the cavity and the saline port, a waste position where the waste passage provides communication between the proximal region of the cavity and the waste port and an injection position where the injection passage provides communication between the proximal region of the cavity and the outlet port.

23. The fluid control apparatus of claim 22 wherein the open proximal end of the body is connected to a syringe.

24. The fluid control apparatus of claim 22 wherein the open proximal end of the body is connected to a pump.

25. The fluid control apparatus of claim 22 wherein the body further comprises a separating wall disposed between the proximal and distal regions of the cavity, the separating wall comprising an aperture providing fluid communication between the proximal and distal regions of the cavity.

* * * * *